United States Patent

Hakamatsuka et al.

[11] Patent Number: 5,152,791
[45] Date of Patent: Oct. 6, 1992

[54] PROSTHETIC ARTIFICIAL BONE HAVING CERAMIC LAYERS OF DIFFERENT POROSITY

[75] Inventors: Yasuharu Hakamatsuka, Akishima; Hiroyuki Irie, Hachioji, both of Japan

[73] Assignee: Olympus Optical Co., Ltd., Tokyo, Japan

[21] Appl. No.: 839,060

[22] Filed: Feb. 18, 1992

Related U.S. Application Data

[63] Continuation of Ser. No. 621,612, Dec. 3, 1990, abandoned.

[30] Foreign Application Priority Data

Dec. 7, 1989 [JP] Japan .................................. 1-318230

[51] Int. Cl.⁵ .............................................. A61F 2/28
[52] U.S. Cl. ...................................................... 623/16
[58] Field of Search ........................................... 623/16

[56] References Cited

U.S. PATENT DOCUMENTS

| | | | |
|---|---|---|---|
| 4,000,525 | 1/1977 | Klawitter et al. | 623/20 |
| 4,237,559 | 12/1980 | Borom | 623/16 |
| 4,330,514 | 5/1982 | Nagai et al. | 623/16 |
| 4,911,720 | 3/1990 | Collier | 623/16 |

OTHER PUBLICATIONS

Synthesis of β-Tricalcium Phosphate by Use of Wet Milling, Motohiro Toriyama and Sukezo Kawamura, Yogyo-Kyokai-Shi 94 [9] 1986, 1004–1008.

*Primary Examiner*—Randy C. Shay
*Attorney, Agent, or Firm*—Frishauf, Holtz, Goodman & Woodward

[57] ABSTRACT

A prosthetic artificial bone having a double-layered structure obtained by forming a high porosity portion having a porosity of from 40 to 90% and a lower porosity portion having a porosity of 50% or less, into an integral body, and wherein the high porosity portion and the lower porosity portion each comprise a ceramics containing calcium and phosphorus.

5 Claims, 1 Drawing Sheet

PROSTHETIC ARTIFICIAL BONE HAVING CERAMIC LAYERS OF DIFFERENT POROSITY

This application is a continuation of application Ser. No. 07/621,612, filed Dec. 3, 1990, now abandoned.

BACKGROUND OF THE INVENTION

1. Field of the Invention

The present invention relates to a prosthetic artificial bone which is used in the medical fields such as orthopaedics, cerebral surgery, oral surgery and dentistry.

2. Description of the Related Art

When the bone is abscised because of fracture, breakage of sinew at arthrosis, arthritis, serious rheumatism and the like, there has been increasingly carried out in the field of orthopaedics to insert and fix an artificial bone into the abscised part for purposes of restoring the function.

The conventional prosthetic member using for the artificial bone and the artificial arthrosis, etc., mainly consists of metal, ceramics or plastics and is fixed to the bone through a bone cement of which major component is methylmethacrylate.

It has been reported, however, that the metallic members are apt to elute into an organism as metal ions or to corrode to give evil influences onto the surrounding biological tissues and that they are likely to be deteriorated in strength and to fracture due to the metal fatigue.

The bone cement has also been reported to have an intrinsic biological harm or to be absorbed over long periods of time in addition to disjunction of the prosthetic member.

Further the ceramic members have been also reported recently that its powder generated by abrasion is apt to give evil influences onto the surrounding biological tissues and to cause loosening and disjunction due to a lack of the connection to the organism. Therefore the development of a prosthetic artificial bone which can overcome the above described problems has been demanded.

SUMMARY OF THE INVENTION

The object of the present invention is to provide a prosthetic artificial bone which is free from a biological harm and can be jointed directly to the bone without a help of a bone cement and can reproduce a cartilaginous tissue.

Said object can be attained by a prosthetic artificial bone having a double-layered structure obtained by molding a porous portion having a porosity of from 40 to 90% and a dense portion having a porosity of not more than 50% into an integral body, wherein both of the porous portion and the dense portion comprise a ceramics containing calcium and phosphorus.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWING

The accompanying drawing, which is incorporated in and constitutes a part of the specification, illustrates a presently preferred embodiment of the invention and, together with the general description given above and the detailed description of the preferred embodiment given below, serves to explain the principles of the invention.

DETAILED DESCRIPTION OF THE PREFERRED EMBODIMENTS

Figure 1:
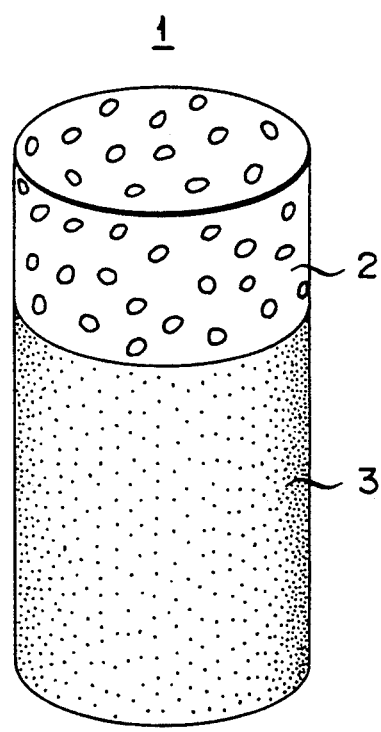
FIG. 1 is a perspective view of one embodiment of the present invention.

The prosthetic artificial bone in accordance with the present invention has a high porosity portion and a denser (lower porosity) portion, which are formed into an integral body. The porous portion is characterized in its faster rate of absorption by an organism while the denser portion has a higher strength. Therefore by arranging said denser portion to be buried into hard tissues such as bone, and said high porosity portion to be brought into contact with cartilage or soft tissues, the formation of a cartilage can be promoted while retaining the strength of the bone portion.

The raw material of the present inventive prosthetic artificial bone is a ceramics containing calcium and phosphorus so that the prosthetic member free from biological harm, which can be connected to the bone without help of a bone cement, can be obtained. Ceramics to be used as a raw material has a mol ratio between calcium and phosphorus (Ca/P ration) of 1.0 to 2.0, and preferably 1.40 to 1.70. Examples of such ceramics may include: ceramics comprising calcium phosphate such as tricalcium phosphate (TCP); and glass containing both calcium and phosphorus, etc. Said calcium phosphate can be prepared by, for example, the wet Milling Method. Also said ceramics may be added by compounds other than calcium and phosphorus. For example, tricalcium phosphate containing hydroxyapatite or β-TCP slightly containing MgO can be used advantageously. More specifically, for the high porosity portion of the present inventive prosthetic artificial bone, the following compounds can be used suitably; a calcium phosphate compound having a Ca/P ratio of from 1.40 to 1.70 produced by the Wet Milling Method, a tricalcium phosphate containing hydroxyapatite (HAP), and a glass containing calcium and phosphorus. In addition, for the denser portion (lower porosity), a calcium phosphate compound having a Ca/P ratio of from 1.40 to 1.70 and produced by the Wet Milling Method; a calcium phosphate compound having a Ca/P ratio of from 1.40 to 1.70 and containing $SiO_2$ together with $Al_2O_3$, also produced by the Wet Milling Method; β-TCP; HAP; a mixture of β-TCP and HAP; a glass containing calcium and phosphorus; or a glass ceramics, can be used advantageously.

The present invention will be explained in detail referring to the following Examples.

EXAMPLE 1

In FIG. 1, there is shown a perspective view of a prosthetic artificial bone of this example. The prosthetic artificial bone 1 has a cylindrical shape of 3 mm in diameter and 10 mm long and is produced by molding a high porosity portion 2 which is formed in the upper part of 2.5 mm long and has a porosity of 75%, and a denser portion 3 which is formed in the lower part of 7.5 mm long and has a lower porosity of 40% or less, into an integral body to constitute a double-layered structure with different porosities.

The preparation method of the prosthetic artificial bone 1 will be described below.

The raw material of powdery β-TCP, which was prepared by a mechanochemical method, was added by water, a foaming agent and a foam stabilizer and the resultant mixture was allowed to foam. Thus, two types of the foamed slurries each having a different degree of foaming were prepared. The slurry to be used for forming a member with a high porosity of 75% (referred to as a 75% slurry) was prepared by mixing 30 g of β-TCP powder with 15 ml of water and 3 ml of a foaming agent together with 15 ml of a foam stabilizer for 2 minutes by means of a mixer then by allowing to foam. The other slurry to be used for forming a member with a lower porosity of 40% (referred to as a 40% slurry) was prepared by mixing 30 g of β-TCP powder with 10 ml of water and 3 ml of a foaming agent together with 6 ml of a foam stabilizer for 2 minutes by means of a mixer then by allowing to foam.

Then the 75% slurry was poured into a cylindrical container followed by a gentle introduction of the 40% slurry so as to form two layers not mingling with each other. The resultant layered slurry was dried for about one day at a temperature of 30 to 40° C. and thereafter sintered for one hour at 1,110° C. to produce a prosthetic artificial bone 1 comprising a β-TCP integrated body having a high porosity portion 2 with a porosity of 75% and a denser (lower porosity) portion 3 with a porosity of 40%.

The thus obtained prosthetic artificial bone 1 was subjected to experiments and the results are as follows.

The articular surface of the tibia of a beagle was bored with a hole in which the prosthetic artificial bone 1 was buried in such an arrangement that the denser portion 3 was locating within the bone, and the thus treated member was observed at the time of 4-week elapse, 8-week elapse, 12-week elapse and 24-week elapse respectively.

In the articular surface, fibrocartilage was formed after 4 weeks, which was grown-up after 8 weeks and even a part of which was changed into a vitreous one to form a vitreous cartilage. After 12 weeks the vitreous cartilage was formed in almost all the articular surface and after 24 weeks vitreous cartilage was completely formed. As is apparent from the above, with the elution of the porous portion 2 the cartilage was restored and reproduced in a shorter period. Furthermore the reproduced cartilage was converted through a fibrocartilage into a vitreous one having a higher strength with the elapse of the buried period. While also the denser portion 3 buried within the bone began to join to the bone after 4 weeks and after 8 weeks not only was it completely jointed to the bone but also a part thereof began to be substituted by the natural bone. After 12 weeks the substitution with the natural bone has been taken place almost in every part and was accomplished at the time of 24-week elapse and the border could hardly be discriminated. As explained above, also in the denser portion 3 a satisfactory junction to the bone as well as the substitution with natural bone can be attained in a shorter period.

Thus the prosthetic artificial bone 1 of this example was confirmed to promote osteogenesis as well as chondrogenesis satisfactorily in a considerably short period.

EXAMPLE 2

The prosthetic artificial bone of this example is the same as that of Example 1 except for materials and porosities of both high porosity and denser portions. Namely, the prosthetic artificial bone of this example was formed with a high porosity portion having a porosity of 80% and comprising a mixture of β-TCP and $Na_2O$-$CaO$-$P_2O_5$-$Al_2O_3$ glass in addition to a denser portion having a porosity of 30%.

The preparation method of the prosthetic artificial bone will be explained below.

A powdery β-TCP synthesized by a mechanochemical method was mixed with a glass powder comprising $Na_2O$, $CaO$, $P_2O_5$ and $Al_2O_3$ in a mole ratio of 10:40:45:5, in a mole ratio of 40:60. To 30 g of thus prepared powdery mixture 16 ml of water, 4 ml of a foaming agent and 17 ml of foam stabilizer were added, and mixed for 2 minutes by means of a mixer. Thereby, the resultant mixture was foamed to give a foamed slurry to be used for forming a member with a high porosity of 80%. Separately 30 g of β-TCP powder were mixed with 10 ml of water, 2 ml of a foaming agent and 17 ml of a foam stabilizer for 2 minutes by means of a mixer and the resultant mixture was allowed to foam to give a slurry used for forming a member with a lower porosity of 30%.

The thus prepared two types of the slurries were gently poured into a cylindrical container just in the same way as in Example 1 so as to form two layers not mingling with each other. The resultant layered slurry was dried for about one day at a temperature of 30 to 40° C., and then sintered for one hour at 1,100° C. to give a prosthetic artificial bone of an integrated body consisting of a high porosity having a porosity of 80% and comprising a mixture of β-TCP and $Na_2O$-$CaO$-$P_2O_5$-$Al_2O_3$ glass, and denser portion having a porosity of 30% and comprising β-TCP.

Thus obtained prosthetic artificial bone was subjected to experiments just in the same way as in Example 1 and satisfactory results were also obtained.

EXAMPLE 3

The prosthetic artificial bone of this example is the same as the above Examples 1 and 2 except for materials and porosities of both the high porosity and denser portions. Namely, the prosthetic artificial bone of this example was formed with a high porosity portion having a porosity of 80% and comprising $Na_2O$-$CaO$-$P_2O_5$-$SiO_2$ glass in addition to a denser portion having a porosity of 50% and comprising β-TCP containing HAP in amounts of 8% by weight.

The preparation method of the prosthetic artificial bone will be explained below.

To 30 g of a glass powder, which were prepared by mixing 46.1 mol % of $Na_2O$, 2.6 mol % of $CaO$, 26.9 mol % of $P_2O_5$ and 24.4 mol % of $SiO_2$ to give a sum total of 100 mol %, 16 ml of water, 4 ml of a foaming agent and 17 ml of a foam stabilizer were added, and mixed for 2 minutes by means of a mixer. Thereby, the resultant mixture was foamed to give a foamed slurry to be used for forming a high porosity member with a porosity of 80%.

Separately, to 30 g of β-TCP powder containing HAP in amounts of 8 wt. %, prepared by a mechanochemical method, 11 ml of water, 3 ml of a foaming agent and 7 ml of a foam stabilizer were added, and mixed for 2 minutes by means of a mixer. Thereby, the resultant mixture was foamed to give a slurry to be used for forming a lower density member with a porosity of 50%.

Thus prepared two types of slurries were gently poured into a cylindrical container just in the same way as in the above Examples so as to form two layers not mingling with each other. Then the resultant layered slurry was dried for about one day at a temperature of 30 to 40° C. and sintered for one hour at 1,100° C. to give a prosthetic artificial bone of an integrated body consisting of a high porosity portion having a porosity of 80% and comprising $Na_2O\text{-}CaO\text{-}P_2O_5\text{-}SiO_2$ glass, and a dense portion having a porosity of 50% and comprising β-TCP containing HAP in amounts of 8 wt. %.

The thus obtained prosthetic artificial bone wa subjected to experiments just in the same way as in the above Examples and satisfactory results were also obtained.

Furthermore the present prosthetic artificial bone was proved to have an improved strength as compared with the above Examples, since β-TCP containing HAP in amounts of 8 wt. % was used as the material of the denser portion to be buried within the bone.

EXAMPLE 4

The prosthetic artificial bone of this example is the same as that of above Examples 1 through 3 except for the materials and porosities of both the high porosity and denser portions. Namely, the prosthetic artificial bone was formed with a high porosity portion having a porosity of 90% and comprising β-TCP containing HAP in amounts of 8 wt. % in addition to a dense portion having a porosity of 50% and comprising β-TCP containing $SiO_2$ in amounts of 3 wt. % and $Al_2O_3$ in amounts of 6 wt. %.

The preparation method of the prosthetic artificial bone will be explained below.

30 g of β-TCP powder containing HAP in amounts of 8 wt. % prepared by a mechanochemical method, 16 ml of water, 5 ml of a foaming agent and 18 ml of a foam stabilizer were added, and mixed for 2 minutes by means of a mixer. Thereby, the resultant mixture was foamed to give a slurry to be used for forming a high porosity member with a porosity of 90%.

Separately, to 30 g of β-TCP powder prepared by a mechanochemical method, which comprises $SiO_2$ in amounts of 3% by weight together with $Al_2O_3$ in amounts of 6% by weight, 11 ml of water, 3 ml of a foaming agent and 7 ml of a foam stabilizer were added, and mixed for 2 minutes by means of a mixer. Thereby, the resultant mixture was foamed to give a slurry to be used for forming a lower porosity member having a porosity of 50%.

The thus prepared two types of slurries were gently poured into a cylindrical container just in the same way as in the above described Examples so as to form two layers not mingling with each other. The resultant layered slurry was dried for about one day at a temperature of 30 to 40° C. and thereafter sintered for one hour at 1,100° C. to give a prosthetic artificial bone of an integrated body consisting of a higher porosity portion having a porosity of 90% and comprising β-TCP containing HAP in amounts of 8 wt. % and a denser portion having a porosity of 50% and comprising β-TCP containing $SiO_2$ in amounts of 3 wt. % and $Al_2O_3$ in amount of 6 wt. %.

The thus obtained prosthetic artificial bone was subjected to experiments just in the same manner as in the above Examples and satisfactory results were also obtained.

Furthermore the present prosthetic artificial bone was proved to have a far more improved strength than those of the above Examples, since β-TCP containing $SiO_2$ in amounts of 3 wt. % and $Al_2O_3$ in amounts of 6 wt. % was used as the material of the denser portion to be buried within the bone.

As has been explained above with reference to Examples, the prosthetic artificial bone in accordance with the present invention has no biological harm and not only can be jointed to the bone directly without using bone cement, but also can promote the reproduction of cartilage-tissue, vitreous cartilage in particular.

What is claimed is:

1. A prosthetic artificial bone, comprising:
   a first end portion having a high porosity of 40 to 90%, said first end portion having an end surface and side wall surfaces which are arranged to be brought into direct contact with a soft body tissue such as cartilage when said artificial bone is implanted into a human body so as to facilitate formation of mainly cartilage; and
   a second end portion having a low porosity of 50% or less, said second end portion having an end surface and side wall surfaces which are arranged to be brought into direct contact with a hard body tissue such as bone when the artificial bone is implanted into the human body so as to facilitate mainly coupling with bone and substitution for bone, the porosity of said second end portion always being lower than that of said first end portion; and
   wherein said artificial bone is an integral double-layer structure consisting of said first and second end portions connected together with said end and side wall surfaces thereof exposed for said direct contact with said soft and hard body tissue respectively, and wherein said double-layer artificial bone structure is made of a ceramic material containing calcium and phosphorus, exhibiting an affinity with a living body, and being absorbed by the living body.

2. A prosthetic artificial bone according to claim 1, wherein said high porosity portion comprises a ceramics selected from the group consisting of a calcium phosphate compound having a Ca/P ratio of from 1.40 to 1.70 prepared by wet milling method, tricalcium phosphate containing hydroxyapatite, and a glass containing calcium and phosphorus.

3. A prosthetic artificial bone according to claim 1, wherein said low porosity portion comprises a ceramics selected from the group consisting of a calcium phosphate compound having a Ca/P ratio of from 1.40 to 1.70 prepared by wet milling method, a calcium phosphate compound having a Ca/P ratio of from 1.40 to 1.70 and containing both $SiO_2$ and $Al_2O_3$ prepared by wet milling method, β-TCP, a mixture of β-TCP and HAP, a glass containing calcium and phosphorus, and a glass ceramics.

4. The prosthetic artificial bone according to claim 1, wherein said ceramic material contains β-TCP which is absorbable within a living body.

5. The prosthetic artificial bone according to claim 4, wherein said first and second end portions are formed of ceramic materials differing from each other only in porosity.

* * * * *